(12) United States Patent
Shiba

(10) Patent No.: US 6,333,193 B1
(45) Date of Patent: Dec. 25, 2001

(54) CELL GROWTH ACCELERATOR AND CELL GROWTH METHOD USING THE SAME

(75) Inventor: Toshikazu Shiba, Sapporo (JP)

(73) Assignee: Nipro Corporation, Osaka (JP)

(*) Notice: Subject to any disclaimer, the term of this patent is extended or adjusted under 35 U.S.C. 154(b) by 0 days.

(21) Appl. No.: 09/384,384

(22) Filed: Aug. 27, 1999

(30) Foreign Application Priority Data

Aug. 28, 1998 (JP) .................................................. 10-242416
Sep. 24, 1998 (JP) .................................................. 10-288869

(51) Int. Cl.⁷ ...................................................... C12N 5/00
(52) U.S. Cl. ............................ 435/405; 435/325; 435/404; 424/601
(58) Field of Search ..................................... 435/325, 404, 435/405; 424/601

(56) References Cited

U.S. PATENT DOCUMENTS 4,115,199 * 9/1978 Porubcan et al. .
4,615,977 * 10/1986 Hasegawa et al. .
5,108,755   4/1992 Daniels et al. .

* cited by examiner

*Primary Examiner*—Leon B. Lankford, Jr.
(74) *Attorney, Agent, or Firm*—Kubovcik & Kubovcik

(57) ABSTRACT

Provided are a cell growth accelerator containing a polyphosphoric acid and a cell growth method in which cells are grown by adding the cell growth accelerator to a medium for cells of animals and plants or by using a glass or plastic cell cultivator containing or coated with the cell growth accelerator. When substances are produced in vitro using culture cells, the cell culture and the cell growth acceleration are conducted at low cost safely and efficiently by adding the cell growth accelerator containing the polyphosphoric acid to the medium for cells of animals and plants or by using the cell cultivator containing or coated with the cell growth accelerator.

9 Claims, 11 Drawing Sheets

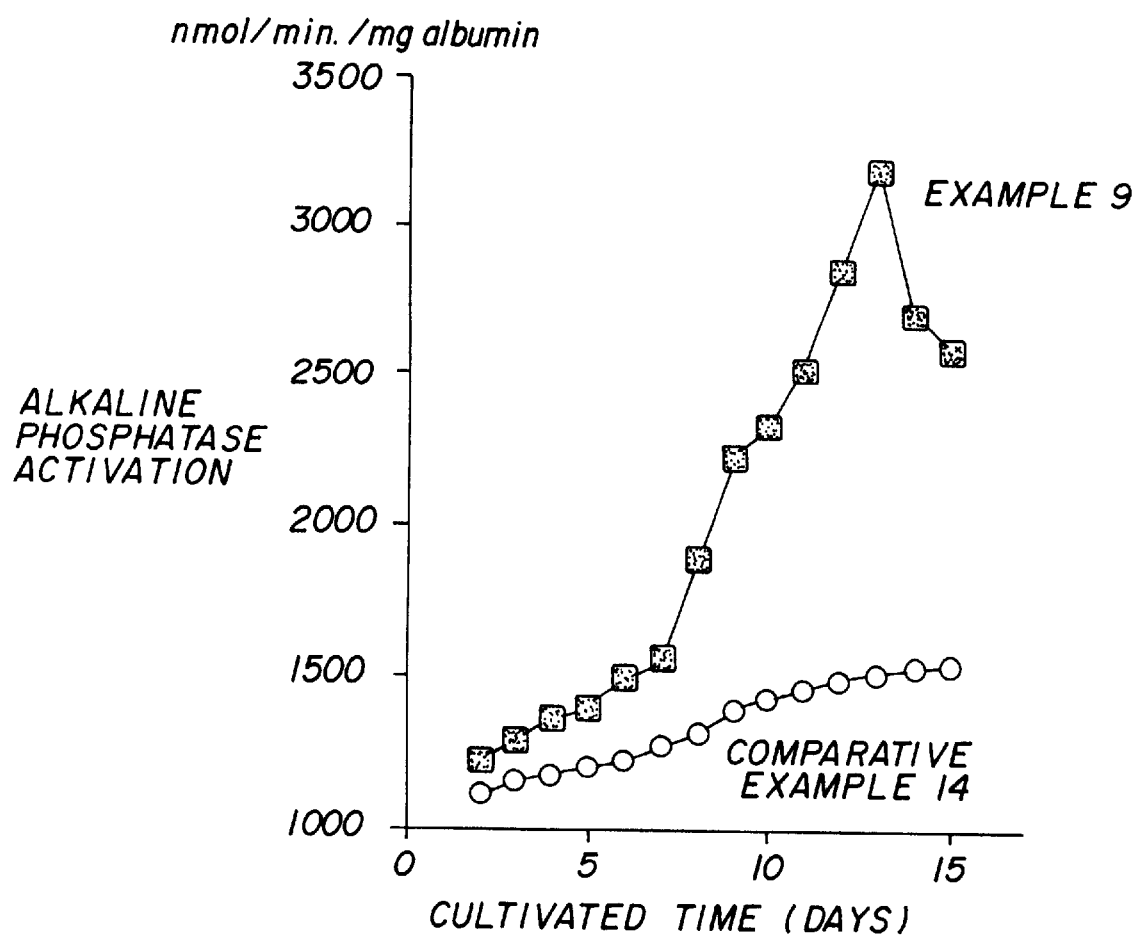

CELL GROWTH ACCELERATOR AND CELL GROWTH METHOD USING THE SAME

FIELD OF THE INVENTION

The present invention relates to a cell growth accelerator and a cell growth method using the same. More specifically, it relates to a cell growth method using a polyphosphoric acid as a cell growth accelerator.

DESCRIPTION OF THE RELATED ART

When animal cells are cultivated in vitro, a medium obtained by adding serum as a cell growth factor in an amount of from 10 to 20% to a basal medium containing amino acids, vitamins, saccharides and inorganic salts has been generally used. However, the serum cannot be mass-produced and is therefore quite expensive, and further, each individual composition (by lot) differs greatly. Since the amount of one lot is limited, intricate procedures such as lot checking, preparation and control of culture conditions are required whenever the lot changes.

In many cases, when substances (particularly, proteins including enzymes, physiologically active substances, vaccines and viruses) are produced using culture cells, serum is required. The development of a technique in which to minimize the amount of serum used or to use a serum-free medium has been underway. Instead of serum, various cell growth factors or hormones, such as pituitary extract, fibroblast growth factors and insulin, are added to a basal medium to expedite the cell growth. However, since growth factors or hormones added instead of serum are expensive, the cost for maintaining culture cells becomes high. Further, there is a likelihood that pathogens such as viruses and prions are incorporated in serum, and contamination with such pathogens is an issue.

Further, various medications have been used for treatment of injuries, burns or wounds in patients undergoing a surgical operation. However, there is no medication to expedite the tissue repair by accelerating the cell growth. Treatment is indirectly expedited by preventing bacterial infection with, for example, antibiotics. In the treatment of burns, an artificial skin effective for expediting regeneration of tissue and accelerating healing has been put to practical use. However, a substance that actively functions, as an ingredient of artificial skin, to expedite the cell growth and accelerate healing has been relatively unknown, except for natural proteins such as collagen. Moreover, in treatment of alveolar pyorrhea, a periodontal disease, material comprising of natural substances, including proteins such as a periodontium regeneration factor, has been under development. Nevertheless, it has not yet been put to practical use.

Furthermore, with respect to the problem of hair growth promotion, various extracts of natural substances, synthetic agents or estrogens, having the functions of hair matrix cell activation and blood flow promotion, have been reported as effective components, and pharmaceuticals or medicated toiletries for hair growth promotion have been provided. For example, a hair growth promotor obtained by mixing a scalp activation promotor (such as camphor, capric acid, phenol or salicylic acid) with an extract of *Houttuynia cordata*, *Artemisia indica* or an aloe is described in JP-A-10-194935. Further, a hair growth promotor containing an extract of *Geranium nepalense* ssp. *thunbergii* as a cell activator is described in JP-A-9-227342. Still further, a product obtained by mixing a blood flow promotor with naphthalenesulfonic acid and/or benzophenonesulfonic acid is described in JP-A-8-40835, and a hair growth promotor containing L-menthol, sodium p-toluenesulfonyl chloroamide, sodium hypochlorite or D-pantothenyl alcohol is described in JP-A-7-53334. Thus, a large number of hair growth promoters have been so far introduced.

However, the effect of hair growth promotion using these hair growth promoters has not necessarily been satisfactory.

SUMMARY OF THE INVENTION

It is an object of the invention to accelerate cell growth in cell cultures safely and efficiently with low cost, using a medium and a cell growth material in which cell growth can be accelerated, when produced in vitro with culture cells.

That is, the invention relates to a cell growth accelerator containing a linear condensed polyphosphoric acid and/or a polyphosphate.

Further, the invention relates to a cell growth accelerator wherein the cells are hair matrix cells.

Furthermore, the invention relates to a cell growth accelerator wherein the cells are bone cells.

Further, the invention relates to a cell growth method wherein a polyphosphoric acid is added to a medium for cells of animals and plants.

Still further, the invention relates to a cell growth method, wherein polyphosphoric acid is added to a medium for cells of animals and plants containing from 0 to 10% serum.

Furthermore, the invention relates to a cell growth method, wherein polyphosphoric acid is added to a medium for cells of animals and plants containing a cell growth factor or/and various physiologically active factors.

Moreover, the invention relates to a cell growth method, wherein the cells are grown in a cell cultivator containing, or coated with, polyphosphoric acid.

BRIEF DESCRIPTION OF THE DRAWINGS

FIGS. 4-1 and 4-2 are photos showing hair growth conditions, after 5 days, of jirds of which the sections of skin from the backs are coated by the methods of Example 7 and Comparative Example 11.

FIGS. 5-1 and 5-2 are photos showing hair growth conditions, after 14 days, of jirds of which the sections of skin from the backs are coated by the methods of Example 7 and Comparative Example 11.

FIGS. 6-1 and 6-2 are photos showing hair growth conditions, after 25 days, of jirds of which the sections of skin from the backs are coated by the methods of Example 7 and Comparative Example 11.

FIGS. 7-1, 7-2, and 7-3 are photos showing hair growth conditions of the sections of skin from the backs of jirds when first coated (day 0) by the methods of Example 8 and Comparative Examples 12 and 13.

FIGS. 8-1, 8-2, and 8-3 are photos showing hair growth conditions, after 10 days, of jirds of which the sections of skin from the backs are coated by the methods of Example 8 and Comparative Examples 12 and 13.

FIGS. 9-1, 9-2, and 9-3 are photos showing hair growth conditions, after 14 days, of jirds of which the sections of skin from the backs are coated by the methods of Example 8 and Comparative Examples 12 and 13.

FIGS. 10-1, 10-2, and 10-3 are photos showing hair growth conditions, after 21 days, of jirds of which the sections of skin from the backs are coated by the methods of Example 8 and Comparative Examples 12 and 13.

FIG. 11 is a graph showing a change in the alkaline phosphatase activation of a sodium polyphosphate and sodium phosphate buffer solution with cultivated time.

DETAILED DESCRIPTION OF THE INVENTION

Figure 1:
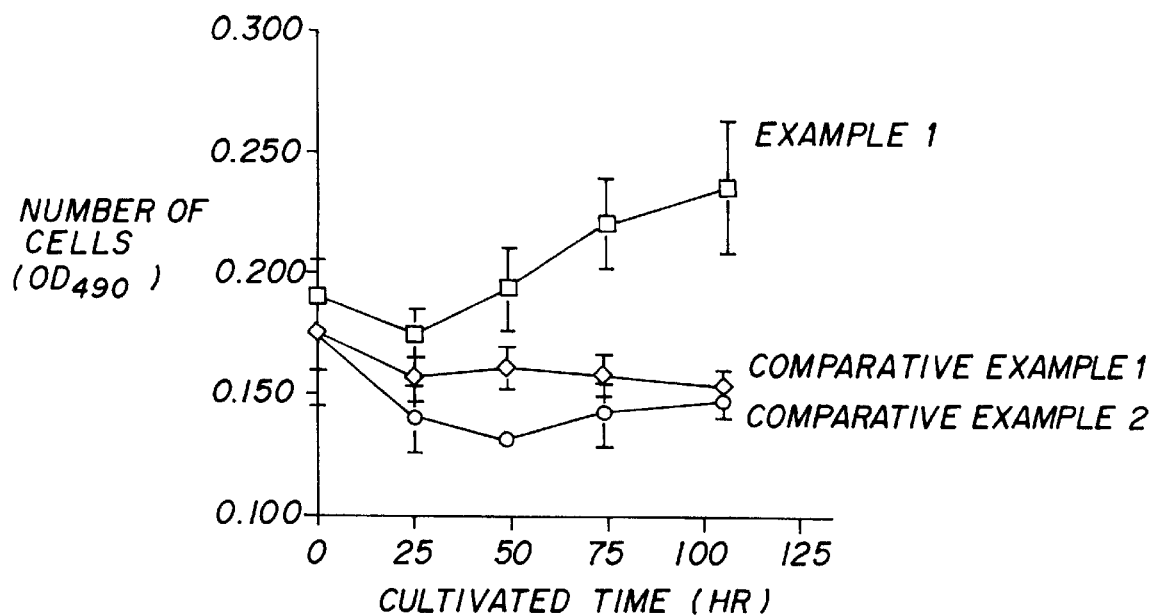
FIG. 1 is a graph showing the change in the growth of human normal epithelial fibroblasts in a medium containing polyphosphoric acid with time.

The polyphosphoric acid useful in the present invention includes a linear condensed polyphosphoric acid obtained through dehydrocondensation of an orthophosphoric acid, a side chain polyphosphoric acid in which an organic group is introduced into a side chain, and a cyclic polyphosphoric acid. Especially preferable is a linear condensed polyphosphoric acid represented by formula $H_{(n+2)}(P_nO_{3n+1})$, wherein n is an integer of at least 2, and it is preferably between 5 and 5,000, more preferably between 15 and 2,000, having a structure in that two or more $PO_4$ tetrahedrons are linearly bound with an oxygen atom held in common. A polyphosphate is a compound having a molecular structure wherein a hydrogen of a hydroxyl group of a polyphosphoric acid is replaced with a metal, such as sodium or potassium. In a phosphoric acid in which n is 1 in the above formula, no effect of the invention is provided. The cell growth accelerator of the invention may contain additives in addition to the polyphosphoric acid.

The polyphosphoric acid stabilizes the cell growth factor which all plant and animal cells secrete in a small amount to accelerate cell growth or to enhance the linkage between cells and the cell growth factor. The polyphosphoric acid promotes activation of hair matrix cells and bring forth hair growth promotion. The amount of the polyphosphoric acid in the hair growth promotor is between $1 \times 10^{-7}$ and 50% by weight, preferably between 0.001 and 10% by weight. When the content of the phosphoric acid is less than $1 \times 10^{-7}$% by weight, no effect of hair growth promotion is observed. When it exceeds 50% by weight, it gives rise to problems with preparation, and the product cannot be used as a hair growth promotor.

Further, in this invention, the polyphosphoric acid is mixed with various substances of which the effect of hair growth promotion has been recognized. That is, the polyphosphoric acid is mixed with at least one agent selected from the group consisting of a cell activator, a blood flow stimulant, a skin stimulant, a humectant and an anti-inflammatory agent.

Examples of a cell activator include panthotenic acid and its derivatives, photosensitive element No. 301, carrot extract, biotin, mononitroguaiacol, allantoin and glyceride pentadecanoate. The amount of the cell activator in the hair growth promotor is preferably between 0.001 and 10% by weight.

Examples of a blood flow stimulant to be mixed with the polyphosphoric acid include acetylcholine, carpronium chloride, extract of Swertia japonica, Guinea pepper tincture, hinokitiol, cepharanthine, benzyl nicotinate, garlic extract, ligusticum extract, gentian extract, γ-oryzanol, licorice, minoxidil, cnidii rhizoma, *Panax japonicus* C. A. Mey, *Panax ginseng* C. A. Mey, ginger, Rhmannia root, aloe, spironolactone, Vitamin B6 hydrochloride, D-camphor, DL-camphor, DL-α-tocopherol, iodized garlic extract, DL-α-tocopherol linoleate, inositol hexanicotinate, Vitamin E derivatives, sodium dextran sulfate, nicotinic acid, DL-α-tocopherol nicotinate, butoxyethyl nicotinate, methyl nicotinate, vanillylamide nonanoate, DL-α-tocopherol succinate, DL-α-tocopherol acetate, cantharis tincture and ginger tincture. The amount of blood flow stimulant is preferably between 0.001 and 10% by weight.

Further, examples of a skin stimulant to be mixed with the phosphoric acid include 1(L)-menthol, peppermint oil, benzyl nicotinate, vanillylamide nonylate and camphor. The amount of a skin stimulant in the hair growth promotor is preferably between 0.001 and 5% by weight.

Still further, examples of a humectant to be mixed with the polyphosphoric acid include glycerin, propylene glycol, hyaluronic acid and its salt, sodium pyrrolidonecarboxylate, chondroitin sulfate, Mini-Sasanishiki extract, vegetative wasp extract and saffron extract. The amount of humectant in the hair growth promotor is preferably between 0.001 and 5% by weight.

Furthermore, examples of an anti-inflammatory agent to be mixed with the polyphosphoric acid include glycyrrhizic acid derivatives, licorice extract, disodium carbenoxolone, guaiazulene, diphenhydramine hydrochloride, lithospermus root extract, rose fruit extract, hydrocortisone acetate and predonisolone. The amount of anti-inflammatory agent in the hair growth promotor is preferably between 0.001 and 3% by weight.

The hair growth promotor of the invention can contain, in addition to these components, an antibacterial agent, a keratolytic agent, an estrogen, an antiseborrheic agent and a nutrient. Examples of an antibacterial agent include benzalkonium chloride, photosensitive element No. 201, a chlorhexidine gluconate solution, chloroxylenol, trichlorocarbanilide, halocarvan and mononitroguaiacol. Examples of a keratolytic acid include salicylic acid, resorcin and lactic acid. Examples of an estrogen include estron, estradiol and ethinyl estradiol. Examples of an antiseborrheic agent include pyridoxine and its derivatives, sulfur, thioxolone, and lecithin. Examples of a nutrient include amino acids, cystine, cysteine, methionine, serine and vitamins.

Moreover, the hair growth promotor of the invention can contain an oil, a surfactant, a polyhydric alcohol, an antioxidant, a metal ion chelating agent, a pigment and a flavor as required. Examples of an oil include isopropylene myristate, lecithin and squalane. Examples of a surfactant include polyoxyethylenesorbitan fatty acid ester, sorbitan fatty acid ester, polyoxyethylene fatty acid ester and glycerin fatty acid ester. Examples of a polyhydric alcohol include propylene if glycol, glycerin and macrogol. Examples of an antioxidant include dibutylhydroxytoluene and isopropyl gallate. Examples of a metal ion chelating agent include ethylenediamine tetraacetate and its salt.

The hair growth promotor of the invention is used by coating a suitable amount thereof one or more times a day on a scalp or a section in which hair growth is expected. The form of the hair growth promotor in the invention is not particularly limited. For example, it can be used as a hair tonic, a hair lotion, a hair cream, an aerosol, an ointment, a shampoo or a hair treatment reagent including a rinse.

As stated above, the polyphosphoric acid incorporated in the hair growth promotor of the invention has an excellent effect on hair growth promotion, particularly in comparison with the conventional product.

Further, the polyphosphoric acid promotes the formation of new bone tissue. Bone morphogenetic protein, a filler for cosmetic surgery, and/or the natural substance containing bone morphogenetic proteins is mixed with a polyphosphoric acid, and the mixture can locally be administered as an implant or a device. In this case, the product to be administered is occluded or injected in a physiologically acceptable viscous form free from a pyrogenic substance and suitable for feeding into a fractured bone site. Consequently, a hard or soft bone structure is formed in the fractured bone site, providing a matrix which can be re-absorbed into the body in an optimum state. The bone regeneration material of the invention is used, as an osterogenic preparation containing the polyphosphoric acid, in preventive applications such as improvements in the reduction of an occlusive fracture or a complicated fracture and the placement of artificial joints.

Further, the osterogenic preparation induces the bone formation and is used in the restoration of an innate or traumatic defective portion or a defective portion caused by a tumor incision.

In vitro, culture cells secrete a trace amount of a cell growth factor in the culture solution. However, under the ordinary incubation conditions, a mixture of a cell growth factor in the form of serum has to be externally supplemented. No efficient growth of cells is observed in a serum-free environment. When polyphosphoric acid is added to a medium for as incubation of cells of animals and plants, cells which ordinarily cannot be grown in a serum-free environment can be grown in the serum-free medium. The cultured cells can be grown in the serum-free free medium or the medium having a low serum concentration by making use of the property of polyphosphoric acid. The concentration of the polyphosphoric acid used in the medium is between 1 nM and 100 mM, preferably between 10 nM and 10 mM.

A serum-free medium obtained by adding polyphosphoric acid to a medium for cells of animals and plants or a medium obtained by adding phosphoric acid and a small amount of serum to a medium for cells of animals and plants is used. The amount of serum added to the medium in the invention is between 0 and 10% by weight, preferably between 0 and 5% by weight. The medium used in the invention can be applied to various culture cells. It can be applied to primary culture cells or strain cells derived from organs such as the liver, the pancreas, the kidney, the lung, the stomach and the spleen, primary culture cells or strain cells derived from leucocytes such as lymphocytes and tissues such as nerves, muscles, skins and bones, and various tumor cells. In this case, the cells referred to include cells of all kinds of organisms including arthropods (insects) and plants as well as embryonic and fetal cells.

Various myeloma cells and hybridoma cells that are commonly used for monoclonal-antibody production, are also applicable. Examples include epithelial keratinocytes, melanocytes, vascular endothelial cells, vascular smooth muscle cells, hair matrix cells, osteoblasts, chondrocytes, amnion cells, fetal kidney cells, fetal lung cells, and strain cells such as Hela cells, FL cells, KB cells, HEp-2 cells, WI-38 cells, MA104 cells, BSC-1 cells, Vero cells, CV-1 cells, BHK-21 cells, RK-13 cells, Raji cells, R388D1 cells, Ralb/3T3 cells, CHO-K1, EB-3, EI-38, HEL cells, hl-60 cells, K562 cells, MPC-11 cells, MRC-5 cells, Namalva cells and L cells. Especially, fibroblast growth factor (FGF) demand cell strains, normal human epithelial fibroblasts, normal human gingival fibroblast cells, normal human epithelial cells and mouse cell strains are preferably used. Polyphosphoric acid can also be applied to cell culture systems preparing a artificial organ, such as an artificial liver, pancreas, skin, etc.

The cell growth factor, which is stabilized with the polyphosphoric acid or of which the linkage with cells is enhanced with the polyphosphoric acid, includes various growth factors. Of these, β-FGF (basic fibroblast growth factor), α-FGF (acidic fibroblast growth factor), FGF-7 (keratinocyte growth factor), PDGF (platelet-derived growth factor), EGF (epidermal growth factor), a vascular endothelial growth factor and pleiotrophine are preferable. These cell growth factors are mixed with the polyphosphoric acid either individually or in combination, and the mixture is added to a medium for animal cell culture to exhibit a high growth acceleration ability compared with that in adding the cell growth factor alone. The concentration of the growth factor used is between 0.1 and 1000 ng/ml depending on the type.

Examples of substances other than the growth factor which accelerate with polyphosphoric acid include all substances that adjust the physiological activity of cells by extracellularly acting on cells (hereinafter referred to as "physiologically active factors"), such as cytokines, a chemotactic factor, hormones, a differentiation inducing factor, a morphogenetic factor, an angiogenetic factor, an angiogenesis inhibitor, a hemopoietic factor, a TGF-β superfamily, TNF, INF and a plant growth factor. These physiologically active factors are mixed with the polyphosphoric acid either individually or in combination, and the mixture is added to a medium for incubation of cells of animals and plants, whereby the growth of culture cells and the control of the physiological activity of cells can be controlled. Substances containing the cell growth factor may be commercial products. The amount of the physiologically active factor is preferably between 1 pg/ml and 1 mg/ml depending on the type.

The medium used in the invention is a medium containing saccharides, amino acids, vitamins and salts, which is ordinarily used to incubate cells of animals and plants. Examples of the medium include Eagle's MEM medium, modified Eagle's MEM medium to which amino acids, vitamins and inorganic salts are added, increased or decreased to adapt to the cells to be incubated, Dulbecco's modified Eagle's medium, Iskov medium, RPMI 1640 medium, Ham F10 medium, Ham F12 medium, MCDB131 medium, MCBD151 medium, MCBD152 medium, MCBD153 medium, MCBD201 medium, MCBD302 medium, GIT medium and MEDIUM199. Further, the medium of the invention may contain additives ordinarily used for cell cultures, such as antibiotics, fungicides, buffers, pigments and agars. Examples of the medium for incubation of plant cells include Murashige and Skoog medium, B5 medium, Nagata and Takebe medium, Kao and Michayluk (8p) medium, Nagy and Maliga (K) medium, Shepard (CL) medium and Chupeau (To).

Examples of the cell incubator used in the invention include a petri dish, a bottle, a flask,.a test tube, a beaker and hollow fibers made of plastics such as polystyrene, polyethylene, polyvinyl chloride, polyester, polycarbonate, acetyl cellulose and polyacrylate and a glass. Either the polyphosphoric acid is added to the incubator materials and the mixture is formed into an incubator, or the surface of the incubator is coated with a film containing the polyphosphoric acid.

The stabilization of the physiologically active factor or the stabilization of the linkage between the cells and the physiologically active factor with the polyphosphoric acid can be applied not only to the culture cells but also to the tissue cells of animals including humans. The polyphosphoric acid stabilizes the functioning of a very small amount of the physiologically active factor which the cells in the tissue secrete, thereby efficiently increasing the growth or the physiological activity of the cells in the tissue and repairing or regenerating the tissue.

The polyphosphoric acid-containing medium and incubator in the invention has properties of accelerating the growth of culture cells in a serum-free state or in a state containing a small amount of a serum or a physiologically active factor, and these can be applied to production of various substances from culture cells. Further, the cell growth accelerator and the pharmaceutical composition containing the polyphosphoric acid accelerate tissue repair and can accelerate the healing of injuries and burns, treatment of periodontal diseases and recovery after surgical operations.

EXAMPLES

The invention is illustrated by the following Examples and Comparative Examples.

Example 1 and Comparative Examples 1 and 2

Normal human epithelial fibroblasts (HF) were spread on a 96-well microtiter plate at a concentration of 5,000 cells/well, and incubated in Eagle's MEM medium containing 10% serum at 37° C. for 24 hours. After the medium was removed through suction, the cells bonded to the plate were washed with PBS (phosphate buffer physiological saline). Serum-free Eagle's medium was added thereto, and the incubation was further conducted for 24 hours. After the completion of the incubation, the medium was removed through suction, and replaced with a culture solution obtained by adding 0.67 mM polyphosphoric acid to Eagle's MEM medium. The subsequent cell growth was measured by the MTS method (CellTiter 96 Non-Radioactive Cell Proliferation Assay Technical Bulletin, #TB112, Promega Corporation). For comparison, the changes in the numbers of cells incubated in the same manner in Eagle's MEM medium containing 0.67 mM phosphate buffer (Comparative Example 1) and in Eagle's MEM medium containing only sterile water (Comparative Example 2) were also measured with time. The results are shown in FIG. 1. In Example 1, a sodium salt was used as the polyphosphoric acid (polyphosphate glass, supplied by Sigma) with an average chain length (number of phosphoric acids) of 65. Further, the phosphate buffer was a sodium salt, and the pH thereof was adjusted to 7.0 as in the medium.

FIG. 1 shows the change in the number of cells incubated in Example 1 with time, and graphically represents the change in the cell growth of human normal epithelial fibroblasts (HF) with time. With respect to the cells incubated in the medium containing the phosphate buffer (Comparative Example 1) and in the medium containing only sterile water (Comparative Example 2), a decrease in the number of cells was observed after the incubation. After 24 hours, almost no growth was observed. Meanwhile, in Example 1 in which the incubation was conducted in the medium containing the polyphosphoric acid, the growth of the cells gradually increased after 24 hours. The acceleration of the cell growth with the polyphosphoric acid was observed for the first 100 hours of the incubation.

Example 2 and Comparative Examples 3 and 4

The experiment was conducted as in Example 1 using human normal gingival fibroblasts. The cell growth was observed in the same manner as in Example 1 except using Dulbecco's modified Eagle's medium. For comparison, the changes with time in the numbers of cells incubated in the same manner in Eagle's MEM medium containing 0.67 mM phosphate buffer (Comparative Example 3) and in Eagle's MEM medium containing only sterile water (Comparative Example 4) were also measured. The results are shown in FIG. 2.

Figure 2:
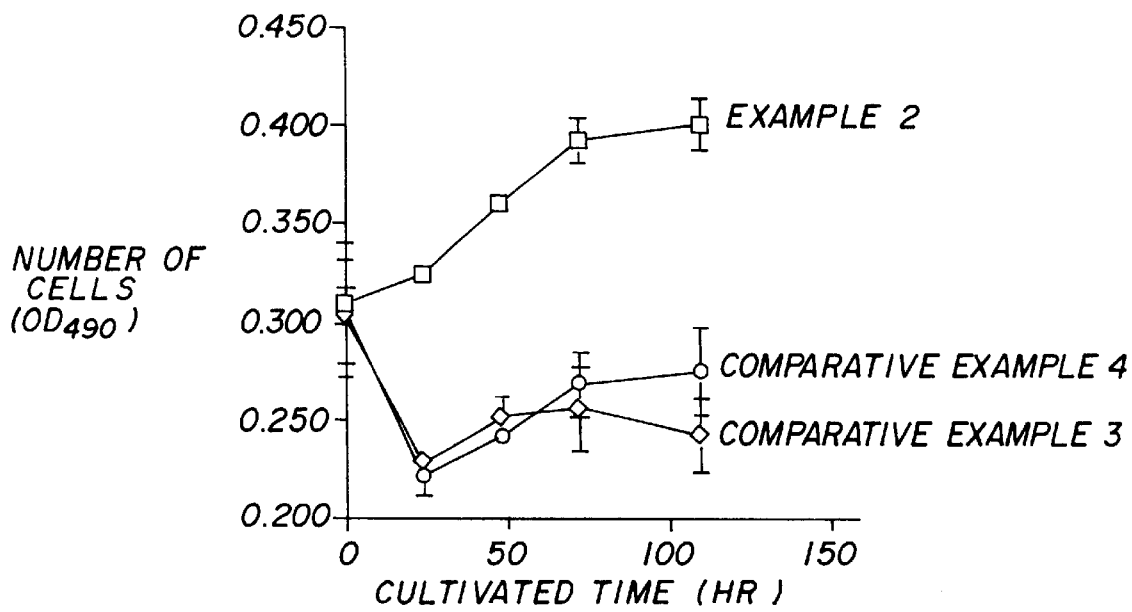
FIG. 2 is a graph showing the change in the growth of normal human epithelial fibroblasts in a medium containing polyphosphoric acid with time.

FIG. 2 shows the results of Example 2, and graphically represents the cell growth of human normal gingival fibroblasts. With respect to the cells incubated in the medium containing the phosphate buffer (Comparative Example 3) and in the medium containing only sterile water (Comparative Example 4), similar to the growth of HF shown in FIG. 1, the number of cells decreased after the incubation. Twenty-four hours later, almost no remarkable growth was observed. Meanwhile, when the incubation was conducted in the medium containing the polyphosphoric acid, the number of cells did not decrease immediately after the beginning of the incubation, and the growth of the cells gradually increased with the lapse of time. The acceleration of the cell growth with the polyphosphoric acid was observed for the first 100 hours of the incubation.

Example 3 and Comparative Examples 5 and 6

Normal human epithelial fibroblasts (HF) were spread on a 12-well microtiter plate at a concentration of $2.5 \times 10^5$ cells/well, and incubated in Eagle's MEM medium containing 10% serum at 37° C. for 24 hours. After the medium was removed through suction, the cells bonded to the plate were washed with PBS (phosphate buffer physiological saline). Serum-free Eagle's medium was added thereto, and the incubation was further conducted for 24 hours. After the completion of the incubation, the medium was removed through suction, and replaced with a culture solution obtained by adding 0.67 mM polyphosphoric acid to Eagle's MEM medium. The subsequent cell growth was measured by counting the number of cells. The number of viable cells after 50 hours of the incubation is shown in Table 1. For comparison, the groups of cells incubated in Eagle's MEM medium containing 0.67 mM phosphate buffer (Comparative Example 5) and in Eagle's MEM medium containing only sterile water (Comparative Example 6) were provided. In Example 3, as in Example 1, a sodium salt was used as the polyphosphoric acid (polyphosphate glass, supplied by Sigma) with an average chain length (the number of phosphoric acids) of 65. Further, the phosphate buffer solution was sodium salt, and the pH thereof was adjusted to 7.0 as in the medium.

TABLE 1

|  | Example 3 | Comparative Example 5 | Comparative Example 6 |
| --- | --- | --- | --- |
| Number of viable cells ($\times 10^5$) | 6.0 | 2.6 | 2.0 |

Table 1 shows the results of Example 3, namely, the cell growth of HF. As is the case with the measurement by the MTS method in Example 1, the increase in the number of cells after the incubation was not observed in the cells incubated in the medium containing the phosphate buffer (Comparative Example 5) and in the medium containing only sterile water (Comparative Example 6). However, the number of cells incubated in the medium containing the polyphosphoric acid increased approximately 2.4 times after 50 hours of incubation.

Example 4 and Comparative Examples 7 and 8

A mouse cell strain, Balb 3T3 was spread on a 96-well microtiter plate at a concentration of 5,000 cells/well, and incubated in Eagle's MEM medium containing 10% serum at 37° C. for 24 hours. After the medium was removed through suction, the cells bonded to the plate were washed with PBS (phosphate buffer physiological saline). Serum-free Eagle's medium was added thereto, and the incubation was further conducted for 24 hours. After the completion of the incubation, the medium was removed through suction, and replaced with Eagle's MEM medium containing 0.67 mM polyphosphoric acid. The subsequent cell growth was measured by the MTS method. Table 2 shows the ratio of the number of cells after 30 hours of the incubation in medium containing polyphosphoric acid (Example 4) to the number of cells after 30 hours of the incubation in a 10% serum-containing medium (Comparative Example 7). The rate of cell growth after 30 hours of the incubation in Eagle's MEM medium containing only sterile water is shown in Table 2 as Comparative Example 8. In Example 4, a sodium salt was used as the polyphosphoric acid with an average chain length (the number of phosphoric acids) of 65. Further, the polyphosphate used was of a sodium salt, and the pH thereof was adjusted to 7.0 as in the medium.

Examples 5 and 6 and Comparative Examples 9 and 10

The experiment was conducted as in Example 4 using a mouse cell strain, Balb 3T3. The incubation of Example 5 was conducted using Eagle's MEM medium containing a mixture of 0.67 mM polyphosphoric acid and 10 ng/ml of an acidic fibroblast growth factor ($\alpha$-FGF) (Example 5). Further, the incubation of Example 6 was conducted using Eagle's MEN medium containing a mixture of 0.67 mM polyphosphoric acid and 10 ng/ml of a basic fibroblast growth factor ($\beta$-FGF) (Example 6). Table 2 shows the ration of the numbers of cells after 30 hours of the incubation in Eagle's MEM medium containing only 10 ng/ml of an acidic fibroblast growth factor ($\alpha$-FGF) (Comparative Example 9) and in Eagle's MEM medium containing only 10 ng/ml of a basic fibroblast growth factor ($\beta$-FGF) (Comparative Example 10) to the number of cells after 30 hours of the incubation in a 10% serum-containing medium (Comparative Example 7). The results are shown in Table 2.

TABLE 2

| CEx. 7 | CEx. 8 | CEx. 9 | CEx. 10 | Ex. 4 | Ex. 5 | Ex. 6 |
|---|---|---|---|---|---|---|
| 1.00 | 0.52 | 0.60 | 0.67 | 0.68 | 0.92 | 1.08 |

CEx.: Comparative Example
Ex.: Example

Table 2 reveals that after 30 hours of the incubation, the growth in the medium containing $\alpha$-FGF and the polyphosphoric acid (Example 5) was approximately 1.5 times that in the medium containing only $\alpha$-FGF (Comparative Example 9). Further, the growth in the medium containing $\beta$-FGF and the polyphosphoric acid (Example 6) was approximately 1.6 times that in the medium containing only $\beta$-FGF (Comparative Example 10). Still further, the acceleration of growth was observed in the medium containing only the polyphosphoric acid. However, when the cell growth factor was combined with the polyphosphoric acid, the highest acceleration of growth was provided.

Example 7 and Comparative Example 11

Figure 3:
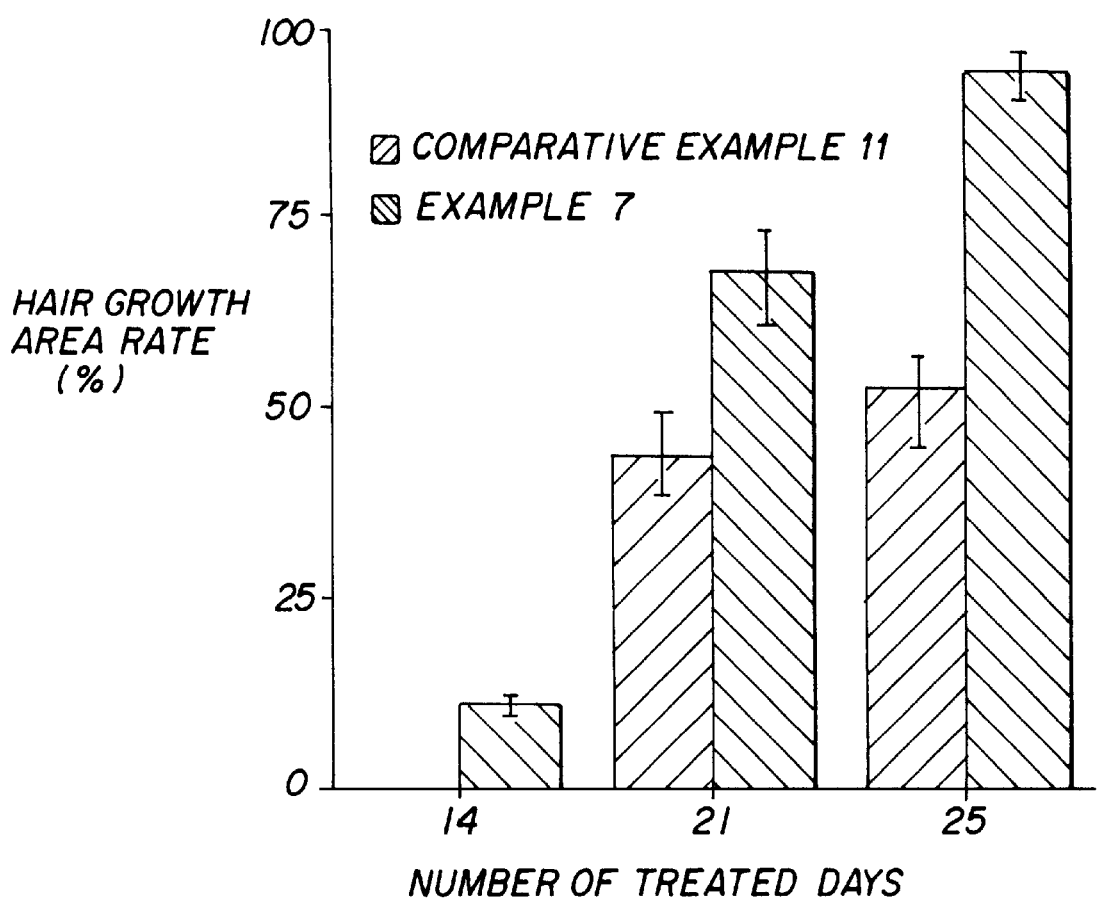
FIG. 3 is a graph showing the change in hair growth area rate (hair growth area/hair-removed area) with time.

The hair on sections of skin from the backs of 7-week-old jirds (male) was cut over an area of approximately 8 cm$^2$ using electric clippers, and completely removed with a depilatory cream. These jirds were divided into two groups each consisting of 10 jirds. Vaseline containing 1% by weight of fine powder of a polyphosphoric acid (the number of phosphoric acid residues—1,000 or more) was coated on the hair-removed section of one group at a dose of approximately 0.2 g each once a day (Example 7). Meanwhile, a mixture of Vaseline with 1% by weight of a fine powder of sodium dihydrogen phosphate and disodium hydrogen phosphate (pH when dissolved in water 7.5) was coated on the hair-removed section of the other group at a dose of 0.2 g each once a day (Comparative Example 11). In order to observe the hair growth condition, the hair-removed section was photographed every day using a digital camera. The image was analyzed using a personal computer to calculate a hair growth area rate (hair growth area/hair-removed area). The change thereof with time is shown in FIG. 3. As is apparent from FIG. 3, the hair growth area rate of jirds in Example 7 of the invention is extremely higher than that of jirds in Comparative Example 11, and it is recognized that the marked effect of hair growth promotion is exhibited in the invention.

Figures 1, 4:
Figures 2, 4:

FIGS. 4-1 and 4-2 are photos showing hair growth conditions, after 5 days, of the jirds of which the sections of skin from the backs were coated by the methods of Example 7 and Comparative Example 11. FIG. 4-1 is a photo in which the section of skin from the back is coated by the method of Example 7, and FIG. 4-2 is a photo in which the section of skin from the back is coated by the method of Comparative Example 7. As is apparent from FIG. 4, the hair growth is clearly observed on the shoulder in the photo of FIG. 4-1 in which the coating is conducted by the method of Example 7 in comparison with FIG. 4-2 in which the coating is conducted by the method of Comparative Example 7.

Figures 1, 5:
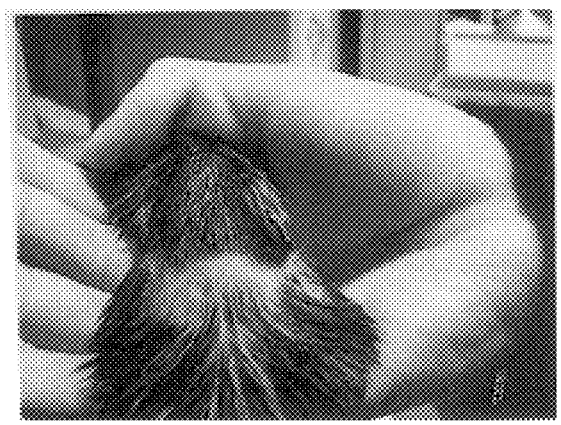
Figures 2, 5:
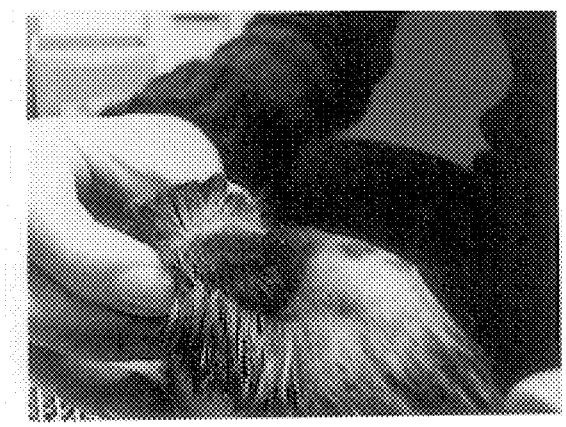

FIGS. 5-1 and 5-2 are photos showing hair growth conditions, after 14 days, of the jirds of which the sections of skin from the backs are coated by the methods of Example 7 and Comparative Example 11. FIG. 5-1 is a photo in which the section of skin from the back is coated by the method of Example 7, and FIG. 5-2 is a photo in which the section of skin from the back is coated by the method of Comparative Example 11. Hair growth is observed on all but the lower section of skin from the back in the photo of FIG. 5-1 in which the coating is conducted by the method of Example 7. Meanwhile, hair growth is observed only on the upper section of skin from the back and not yet observed on the central and lower sections of skin from the back in the photo of FIG. 5-2 in which the coating is conducted by the method of Comparative Example 11.

Figures 1, 6:
Figures 2, 6:

FIGS. 6-1 and 6-2 are photos showing hair growth conditions, after 25 days, of the jirds of which the sections of skin from the backs are coated by the methods of Example 7 and Comparative Example 11. FIG. 6-1 is a photo in which the section of skin from the back is coated by the method of Example 7, and FIG. 6-2 is a photo in which the section of skin from the back is coated by the method of Comparative Example 11. Hair growth is observed on the whole section of skin from the back in the photo of FIG. 6-1 in which the coating is conducted by the method of Example 7. Meanwhile, hair growth is not yet observed on the central section of skin from the back in the photo of FIG. 6-2 in which the coating is conducted by the method of Comparative Example 7.

As is apparent from FIGS. 4 to 6, the marked effect of hair growth promotion is observed in the jirds treated with the polyphosphoric acid of the invention in Example 7 in comparison with the jirds treated with the phosphate in Comparative Example 11.

Example 8 and Comparative Examples 12 and 13

The hair on sections of skin from the backs of 7-week-old jirds (male) was cut over an area of approximately 8 cm$^2$ using electric clippers, and completely removed with a depilatory cream. These jirds were divided into three groups each consisting of 5 jirds. Vaseline containing 1% by weight of fine powder of a polyphosphoric acid (the number of phosphoric acid residues—1,000 or more) was coated on the hair-removed section of one group (Example 8) at a dose of approximately 0.2 g each once a day. Further, only vaseline was coated on the hair-removed section of another group (Comparative Example 12) at a dose of about 0.2 g each once a day. The other remaining group (Comparative Example 13) was untreated, and grown under the same conditions as in the above-mentioned two groups. In order to observe the hair growth conditions, the hair-removed sections were photographed every day using a digital camera, and the images were recorded. The photos thereof are shown in FIGS. 7 to 10.

Figures 1, 7:
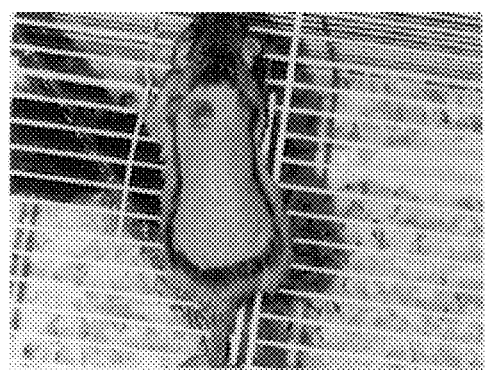
Figures 2, 7:
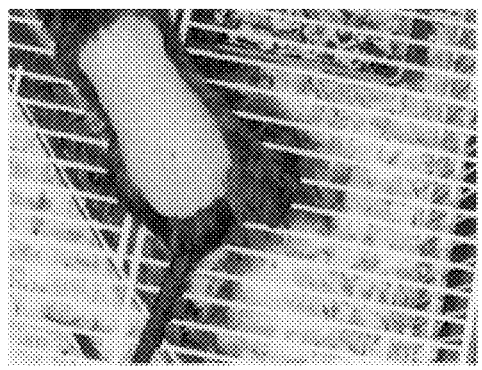
Figures 3, 7:
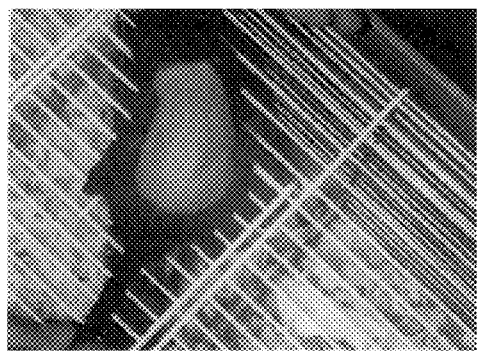

FIGS. 7-1, 7-2 and 7-3 are photos showing hair growth conditions on the sections of skin from the backs of the jirds when coated first (day 0) by the methods of Example 8, Comparative Example 12 and Comparative Example 13. FIG. 7-1 is a photo in which the section of skin from the back is coated by the method of Example 8, and FIG. 7-2 is a photo in which the section of skin from the back is coated by the method of Comparative Example 12. FIG. 7-3 is a photo in which the section of skin from the back is untreated in Comparative Example 13. As is apparent from FIG. 7, the hair growth is not yet observed in any of these cases.

Figures 1, 8:
Figures 2, 8:
Figures 3, 8:

FIGS. 8-1, 8-2, and 8-3 are photos showing hair growth conditions, after 10 days, of the jirds of which the sections of skin from the backs are coated by the methods of Example 8, Comparative Example 12 and Comparative Example 13. FIG. 8-1 is a photo in which the section of skin from the back is coated by the method of Example 8. FIG. 8-2 is a photo in which the section of skin from the back is coated by the method of Comparative Example 12. FIG. 8-3 is a photo in which the section of skin from the back is untreated in Comparative Example 13. As is apparent from FIG. 8, the upper section of skin from the back is blackish and the hair growth is slightly observed in the photo of FIG. 8-1, whereas only the side section of skin from the back is blackish and the hair growth is not yet observed in the photo of FIG. 8-2. The section of skin from the back is only slightly blackish and the hair growth is not yet observed in the photo of FIG. 8-3 in which the jird is untreated in Comparative Example 13.

Figures 1, 9:
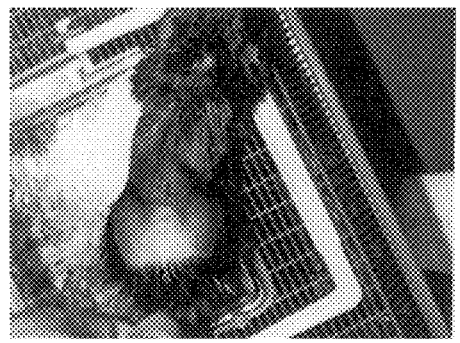
Figures 2, 9:
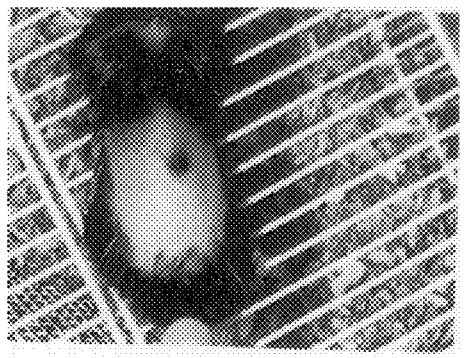
Figures 3, 9:
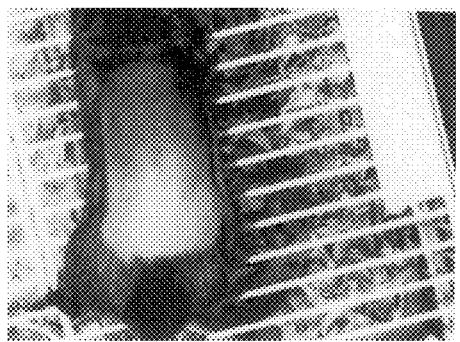

FIGS. 9-1, 9-2, and 9-3 are photos showing hair growth conditions, after 14 days, of the jirds of which the sections of skin from the backs are coated by the methods of Example 8, Comparative Example 12 and Comparative Example 13. FIG. 9-1 is a photo in which the section of skin from the back is coated by the method of Example 8. FIG. 9-2 is a photo in which the section of skin from the back is coated by the method of Comparative Example 12. FIG. 9-3 is a photo in which the jird is untreated in Comparative Example 13. Hair growth is observed on approximately 80% of the section of skin from the back in the photo of FIG. 9-1 in which the coating is conducted by the method of Example 8. Meanwhile, approximately 80% of the section of skin from the back is blackish but the hair growth is not yet observed in the photo of FIG. 9-2 in which the coating is conducted by the method of Comparative Example 12. Further, only the upper section of skin from the back is blackish and the hair growth is not observed in the photo of FIG. 9-3 in which the jird is untreated in Comparative Example 13.

Figures 1, 10:
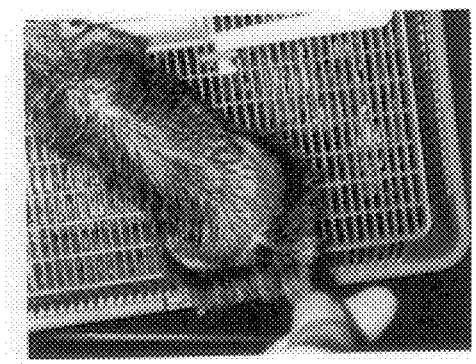
Figures 2, 10:
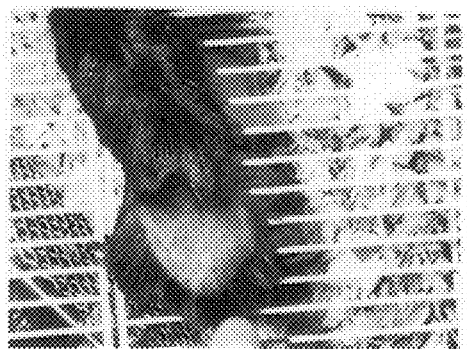
Figures 3, 10:
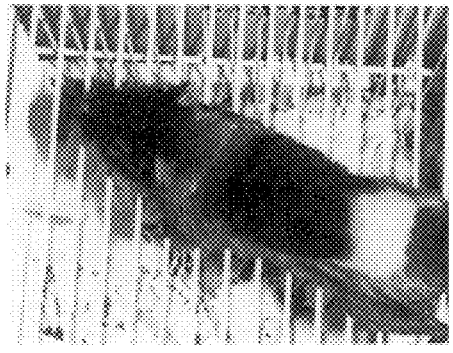

FIGS. 10-1, 10-2, and 10-3 are photos showing hair growth conditions, after 21 days, of the jirds of which the sections of skin from the backs are coated by the methods of Example 8, Comparative Example 12 and Comparative Example 13. FIG. 10-1 is a photo in which the section of skin from the back is coated by the method of Example 8. FIG. 10-2 is a photo in which the section of skin from the back is coated by the method of Comparative Example 12. FIG. 10-3 is a photo in which the section of skin from the back is untreated in Comparative Example 13. Hair growth is observed on the whole section of skin from the back in the photo of FIG. 10-1 in which the coating is conducted by the method of Example 8. Meanwhile, hair growth is not observed in the lower section of skin from the back in the photo of FIG. 10-2 in which the coating is conducted by the method of Comparative Example 12. Further, only approximately 80% of the section of skin from the back is blackish and some hair growth is observed but, on approximately 20% of the back, no effects of hair growth are observed in the photo of FIG. 10-3 in which the jird is untreated in Comparative Example 13.

As is apparent from FIGS. 7 to 10, the jirds treated with the polyphosphoric acid of the invention in Example 8 exhibit a marked effect of hair growth promotion in comparison with the jirds treated with Vaseline alone in Comparative Example 12 and the untreated jirds in Comparative Example 13.

Example 9

The normal human osteoblast cell (manufactured by Bio Whittaker Co.) was cultivated so as to confirm the effect of polyphosphate on bone differentiation. The experiment was conducted in-vitro in a series measuring the alkaline phosphatase activation that showed the indication how the bone cells were accelerated to differentiate with the adding polyphosphoric acid.

It is well known that the alkaline phosphatase activation of is osteoblast cells rise when the cells form new bone. And the rise of this activation indicates the formation of new bone. Normal human osteoblast cells were scattered 10,000 cells/cm$^2$ into a total of fourteen 35 mm culture dishes and were cultivated for 48 hrs. in Osteoblast Basal Medium (manufactured by Bio Whittaker Co.) including fetal bovine serum. After that, the cultivated solution including 1 mM sodium polyphosphate (having an average chain length of 75) was exchanged for the Osteoblast Basal Medium. The alkaline phostase activation of cells from one dish was measured each of 14 days. Also, the cultivated solution including polyphosphoric acid in the remaining dishes was exchanged every three days after starting the measure.

The alkaline phosphatase activation was measured by the following method.

After the cells were washed with PBS [a mixed solution of 20 mM NaPO$_4$ buffer solution (pH 7.0) and 150 mM NaCl], the cells were scaled off by trypsin EDTA from the dish and were suspended in PBS. The cells were separated by a centrifugation and a supernatant was removed. One ml of the solution including the cells was suspended in TBS [a mixed solution of 20 mM Tris-HCl (pH 7.5) and 150 mM NaCl]. After the cells were oscillated by the sonic oscillator, this suspension was centrifuged again and the supernatant was used as a crude enzyme solution. A protein concentration in the crude enzyme solution (A) was measured by using the BIORAD protein assay kit (manufactured by BIORAD). Next, a proper volume of crude enzyme solution was added in a substrate solution that mixed 1.2M Tris-HCl (pH 8.2) and 20n mM p-Nitrophenyl phosphate disodium at the ratio of 1 to 1 and reacted at 28° C. for a fixed number of hours (Δt). After the reaction stopped by adding 2M K$_2$HPO$_4$, the 410 nm absorbance of the reaction solution (B) was measured. The alkaline phosphatase activation was calculated according to the following formula.

$$\text{Alkaline phosphatase activation} = \frac{B}{\Delta t} \times \frac{1}{A} \times \frac{1}{0.015}$$

FIG. 11 shows the change in the alkaline phosphatase activation of sodium polyphosphate with cultivated time.

Comparative Example 14

Sodium phosphate buffer solution was used in place of the sodium polyphosphate used in Example 9. The alkaline phosphatase activation was measured by adding the same concentration of sodium phosphate as in Example 9 to convert polyphosphoric acid into phosphoric acid in the cultivated solution and cultivating for a fixed time.

Example 10 and Comparative Examples 15–18

Figure 12:
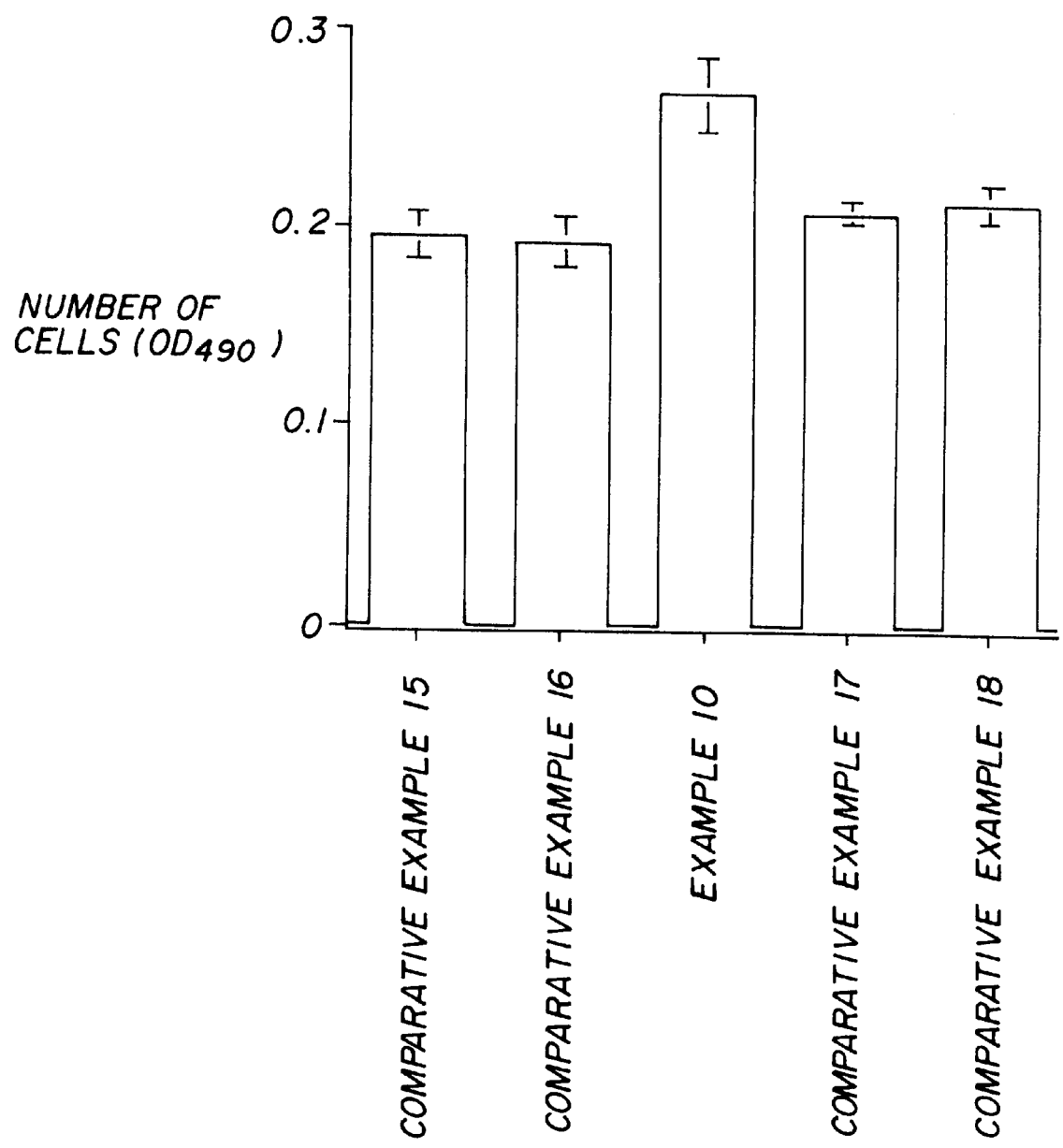
FIG. 12 is a graph showing the cell growth after 72 hours incubated under various condition.

Human hair dermal papilla cells were spread on a 96-well microtiter plate at a concentration of 1,000 cells/well, and incubated with Papilla Cell Growth Media (PCGM) (Toyobo Co.) containing 1% fetal calf serum (FCS) and 1% bovine pituitary extract (BPE) at 37° C. for 24 hours. After the medium was removed through suction, the cells bounded to the plate were washed with phosphate buffer physiological saline. PCGM containing 0.5% FCS was added thereto, and the incubation was further conducted for 24 hours. After the completion of the incubation, the medium was removed through suction, and replaced with PCGM containing 0.5% FCS and 0.67 mM polyphosphoric acid. The subsequent cell growth was measured by the MTS method (CellTiter 96 Non-Radioactive Cell Proliferation Assay Technical Bulletin, #TB112, Promega Corporation) after 72 hours of incubation. As comparative examples, cell growth was monitored by incubating with PCGM containing 0.5% FCS (Comparative Example 15), with PCGM containing 0.5% FCS and 0.67 mM phosphate buffer (Comparative Example 16), with PCGM containing 0.5% FCS and 50 nM pentadecanoic acid (Comparative Example 17), and with PCGM containing 0.5% FCS and 500 nM pentadecanoic acid (Comparative Example 18). The cell growth after 72 hours incubation with various conditions was shown in FIG. 12. The rate of cell growth incubated with poly phosphoric acid is about 1.4-fold greater than that of cell growth incubating with PCGM containing 0.5% serum (Comparative Example 15). No obvious growth stimulation was observed by incubating with phosphate buffer (Comparative Example 16) or pentadecanoic acid (Comparative Examples 17 and 18). In Example 10, a sodium salt was used as the polyphosphoric acid, and its average chain length (the number of phosphoric acid) was 65.

Further, the phosphate buffer used was also of a sodium salt, and the pH thereof was also adjusted to 7.0 as in the medium.

FIG. 11 shows the change in the alkaline phosphatase activation of sodium phosphate buffer solution with cultivated time.

As is evident from FIG. 11, enzyme activation increases remarkably in the cells of Example 9 treated with polyphosphoric acid after 1 week. But, the cells of Comparative Example 14 treated with phosphoric acid buffer solution did not increase remarkably in enzyme activation. The addition of polyphosphoric acid in the cells shows acceleration in the differentiation of bone cells (formation of bone).

What is claimed is:

1. A cell growth accelerator composition comprising a linear condensed polyphosphoric acid represented by the formula:

$$H_{(n+2)}P_nO_{(3n+1)}$$

wherein n is an integer of between 5 and 5,000, a cell growth factor, and a cell growth medium for exposing cells to said cell growth accelerator composition.

2. The cell growth accelerator composition of claim 1, wherein the polyphosphoric acid is a polyphosphate.

3. The cell growth accelerator composition of claim 1, wherein the cells are hair matrix cells.

4. The cell growth accelerator composition of claim 1, wherein said cell growth accelerator composition accelerates bone differentiation.

5. A cell growth method comprising the steps of adding a linear condensed polyphosphoric acid represented by the formula:

$$H_{(n+2)}P_nO_{(3n+1)}$$

wherein n is an integer of between 5 and 5,000, to a cell growth medium containing a cell growth factor and cultivating cells of animals and plants in said medium.

6. The cell growth method of claim 5, wherein the concentration of the polyphosphoric acid added to the medium for cells of animals and plants is between 1 nM and 100 mM.

7. The cell growth method of claim 5, wherein the polyphosphoric acid is added to a medium for cells of animals and plants containing from 0 to 10% of a serum.

8. The cell growth method of claim 5, wherein the polyphosphoric acid is added to a medium for cells of animals and plants containing a physiologically active factor.

9. A cell growth method comprising the step of growing cells in a cell cultivator containing or coated with a linear condensed polyphosphoric acid represented by the formula:

$$H_{(n+2)}P_nO_{(3n+1)}$$

wherein n is an integer of between 5 and 5,000.

* * * * *